United States Patent

Hardtmann et al.

[11] 4,017,499
[45] Apr. 12, 1977

[54] 6H(1)-BENZOPYRANO(3,2-c)QUINOLINES

[75] Inventors: Goetz E. Hardtmann, Morristown; Gary M. Coppola, Parsippany, both of N.J.

[73] Assignee: Sandoz, Inc., E. Hanover, N.J.

[22] Filed: Apr. 5, 1976

[21] Appl. No.: 673,743

[52] U.S. Cl. .................... 260/289 C; 260/296 H; 425/258

[51] Int. Cl.² ...................... C01D 215/16

[58] Field of Search .............. 260/289 C

[56]  References Cited
UNITED STATES PATENTS 2,985,649   5/1961   Lombardi et al. .......... 260/289 C Primary Examiner—Donald G. Daus
Assistant Examiner—David B. Springer
Attorney, Agent, or Firm—Gerald D. Sharkin; Richard E. Vila

[57] ABSTRACT

Anti-inflammatory agents of the formula:

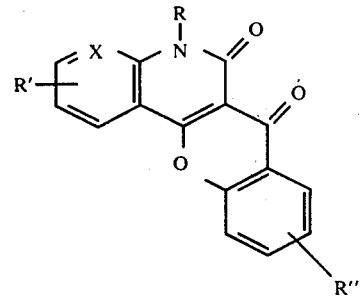

wherein R is lower alkyl, lower alkenyl, lower alkynyl, benzyl, alkyl or halo-substituted benzyl or cycloalkylalkyl, X is CH or N, R' is hydrogen, halo, lower alkyl or lower alkoxy when X is CH and hydrogen and alkyl when X is N, and R" is hydrogen or lower alkyl.

14 Claims, No Drawings

6H(1)-BENZOPYRANO(3,2-c)QUINOLINES

The present invention relates to tetracyclic compounds which are 6H[1]-benzopyrano[3,2-c]quinoline-6,7-(5H)-diones, and to their preparation. The invention also relates to pharmaceutical methods and compositions for utilizing the compounds based on their biological activity.

The present invention provides compounds which may be represented by the structural formula I:

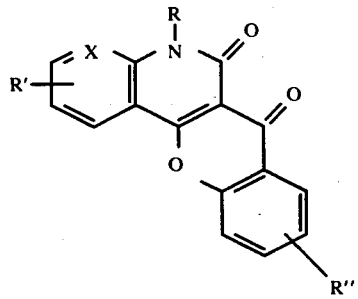

wherein

R is alkyl of 1 to 5 carbon atoms, alkenyl of 3 to 5 carbon atoms, e.g., allyl and methallyl, alkynyl of 3 to 5 carbons, e.g., propargyl, benzyl optionally mono- or disubstituted independently by fluoro, chloro or alkyl of 1 to 4 carbon atoms or cycloalkylalkyl in which the cycloalkyl is of 3 to 6 carbon atoms and the alkyl is of 1 to 3 carbon atoms, X is CH or N, R' is hydrogen, alkyl of 1 to 4 carbon atoms, halo of atomic weight of from 18 to 80, i.e., fluoro, chloro or bromo, or alkoxy of 1 to 4 carbon atoms when X is CH and hydrogen or alkyl of 1 to 4 carbon atoms when X is N, and R'' is hydrogen or alkyl of 1 to 4 carbon atoms.

When R is alkenyl or alkynyl the unsaturation is other than the alpha carbon atom.

The compounds of the formula I may be prepared by a Process A which involves reacting a compound of the formula II:

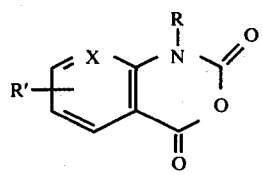

wherein R, R' and X are as above defined, with a compound of the formula III:

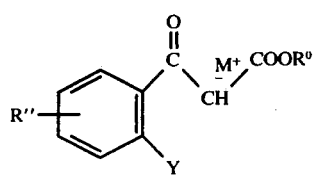

wherein R'' is as above defined, R° is alkyl of 1 to 4 carbon atoms, preferably ethyl, Y is halo of atomic weight of from 18 to 127, preferably fluoro, and M is an alkali metal, preferably sodium, in an inert organic solvent.

Process A may be carried out at temperatures in the range of from 40° to 160° C., preferably 80° to 140° C. Suitable inert organic solvents for the reaction include dimethylacetamide, dimethylformamide and the like, preferably dimethylacetamide. Reaction times are typically of the order of from 2 to 25 hours, more usually 8 to 20 hours.

The compound of the formula III is tautomeric and may be alternately expressed by the formula IIIa:

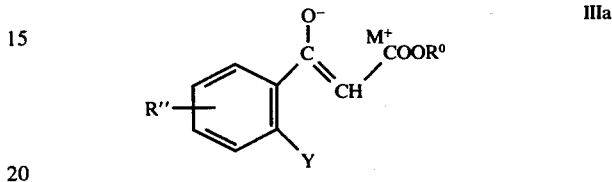

wherein R'', R°, Y and M are as defined. The compound III (or IIIa) is employed in Process A in the form of a solution in an inert organic solvent which is itself useful for conducting Process A. Accordingly, the compound III (or IIIa) is prepared conveniently by reacting a compound of the formula IV:

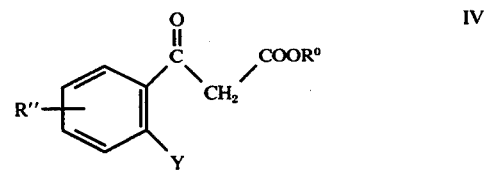

wherein R'', R° and Y are as defined, with a strong base in an inert solvent suitable for use in Process A. Reaction temperatures may be generally of the order of from 0° to 150° C., preferably 50° to 130° C., with the reaction usually initiated at about room temperature and completed by heating to above about 100° C. for a short time. Suitable strong bases include the alkali metal hydrides, e.g., sodium hydride, and the alkali metal alkoxides such as potassium t-butyloxide. The resulting compound of the formula III (or IIIa) in the organic solvent in which it is found is used directly in Process A by mixing with compound II or a solution of compound II.

The reaction product of the formula I may be recovered from the reaction mixture of Process A by working up by established procedures.

The compounds of the formulae II and IV are each either known or may be prepared by established procedures for preparing the known compounds.

The compounds of formula I are useful because they possess pharmaceutical activity in animals. In particular, the compounds I in which R is other than a benzyl radical are useful as anti-inflammatory agents as indicated by the Carrageenan induced edema test in rats (10-150 mg./kg. p.o.). For the above-mentioned use, the dosage administered will, of course, vary depending upon known factors such as the particular compound used and mode of administration. However, in general, satisfactory results are obtained when administered orally at a daily dosage of from about 3 milligrams to about 200 milligrams per kilogram of body weight, preferably given in divided doses 3 to 4 times a day, or in sustained release form. For most mammals, the administration of from about 200 milligrams to about 2000 milligrams of the compound per day provides satisfactory results and dosage forms suitable for internal administration comprise from about 50 milligrams to about 1000 milligrams of the compound in admixture with a solid or liquid pharmaceutical carrier or diluent.

The compounds of the formula I in which R is other than alkenyl and alkynyl are also useful in the treatment of allergic conditions, such as allergic asthma, as indicated by their histamine-release inhibiting activity in the passive cutaneous anaphylaxis test in the rat. Female rats (180–200 g) are sensitised by intramuscular administration of 2 mg of egg albumin (Merck Nr. 967) dissolved in 0.1 ml of physiological saline and 0.5 ml of Haemophilus-pertussis vaccine (Schweizerisches Serum and Impfinstitut, Bern; Nr. 115 325; 4 × 10$^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:2 diluted serum per injection site) at four sites on the backs of untreated, female rats. Twenty-four hours later each rat is administered 32 mg/kg of the test compound, intraperitoneally or orally, as a suspension in tragacanth and either 5 or 30 minutes afterwards, in the case of intraperitoneal administration, or 60 minutes afterwards, in the case of oral administration afterwards egg albumin (5 mg/kg i.v.) dissolved in physiological saline containing 0.25% Evans Blue dye (Merck Nr 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the areas of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

For the above-mentioned use as anti-allergic agents, the dosage administered will, of course, vary depending on the compound employed, mode of administration and treatment desired. However, in general, satisfactory results are obtained upon administration at a daily dosage of from about 0.1 to 50 mg/kg of animal body weight, conveniently given in divided doses two to four times daily, or in sustained release form. For the larger mammals, the total daily dosage is in the range of from about 10 to 400 mg., and dosage forms suitable for oral administration comprise from about 2.5 to 200 mg. of the compound admixed with a solid or liquid pharmaceutical carrier or diluent.

For the above usage, oral administration with pharmaceutically acceptable carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents, and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g. calcium carbonate, calcium phosphate and kaolin. The preferred pharmaceutical compositions from the standpoint of preparation and ease of administration are solid compositions, particularly hard-filled capsules and tablets.

A representative formulation for use in the treatment of inflammation by administration four times a day is a capsule prepared by conventional techniques and containing the following ingredients:

| Ingredients | Part by Weight (mg.) |
| --- | --- |
| 5-methyl-6H[1]-benzopyrano[3,2-c] quinoline-6,7-(5H)-dione | 60 |
| Inert solid diluent e.g., kaolin | 200 |

Preferred compounds of formula I, from the point of view of anti-inflammatory activity, are those in which R is alkyl or cycloalkylalkyl and/or X is CH, more preferably those in which R is alkyl or cyclopropylmethyl and X is CH. Preferred compounds from the standpoint of anti-allergic activity are those in which R is alkyl or benzyl optionally monosubstituted by fluoro, chloro or methyl, more preferably alkyl, with X being CH or N, e.g., the compounds of Examples 2 and 3B hereinafter.

A representative formulation for use in the treatment of allergic asthma by administration four times a day is a capsule prepared by conventional techniques and containing the following ingredients:

| Ingredients | Parts by Weight (mg.) |
| --- | --- |
| Compound of Example 2 or 3B hereinafter | 30 |
| Inert solid diluent, e.g, Kaolin | 200 |

The preferred subject matter provided by this invention is deemed to relate anti-allergic activity and the compounds useful therefor.

EXAMPLE 1

5-Methyl-6H[1]-benzopyrano[3,2-c]quinoline-6,7-(5H)-dione.

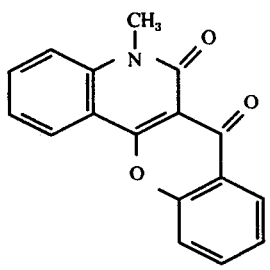

To a solution of 10.5 g. of ethyl o-fluorobenzoyl acetate in 50 ml. of dimethylacetamide is added portion-wise 2.1 g. of sodium hydride (pentane washed) and the resulting mixture stirred at room temperature for 15 minutes and then at 120° C. for 5 minutes. To the resulting mixture is added dropwise a solution of 8.9 g. of N-methyl isatoic anhydride in 50 ml. of dimethylacetamide. The resulting mixture is stirred at 120° C. for 18 hours. The dimethylacetamide is then stripped off and water added to obtain an oily solid which is extracted into methylene chloride, washed with saturated sodium chloride solution, dried and diethyl ether added in exchange for the methylene chloride to yield the title compound, m.p. 302°–304° C.

EXAMPLE 2

5-Methyl-6H[1]-benzopyrano[3,2-c][1,8]naphthyridine-6,7-(5H)-dione.

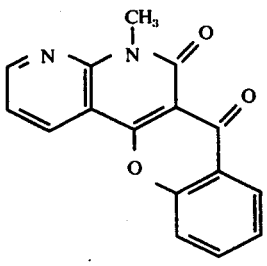

To a solution of 7.0 g. of ethyl o-fluorobenzoyl acetate in 50 ml. of dimethyl acetamide is added portion-wise 1.6 g. of sodium hydride (pentane washed) and the resulting mixture stirred at room temperature for 15 minutes and then at 120° C. for 5 minutes. To the resulting mixture is added dropwise a solution of 5.9 g. of 4-methyl-3,4-dihydro-1,3-dioxo-1H-pyrido[2,3-d][1,3]oxazine in 50 ml. of dimethylacetamide. The resulting mixture is stirred at 120° C. for 15 hours. The reaction mixture is then cooled and the resulting precipitate is recovered by filtering and washed with ethanol and then either and then recrystallized from methylene chloride by the addition of ethanol to yield the title compound, m.p. 307°–310° C.

EXAMPLE 3

Following the procedure of Examples 1 and 2 the following compounds of the invention are prepared:

A. 2-chloro-5-methyl-6H[1]-benzopyrano[3,2-c]quinoline-6,7-(5H)-dione, m.p. 293°–295° C.

B. 5-ethyl-6H[1]-benzopyrano[3,2-c]quinoline-6,7-(5H)-dione, m.p. 266°–269° C.

C. 5-allyl-6H[1]-benzopyrano[3,2-c]quinoline-6,7-(5H)-dione, m.p. 238°–240° C.

D. 5-cyclopropylmethyl-6H[1]-benzopyrano[3,2-c]quinoline-6,7-(5H)-dione, m.p. 232°–235° C.

E. 5-propargyl-6H[1]-benzopyrano[3,2-c]quinoline-6,7-(5H)-dione.

F. 5-isopropyl-15-methyl-6H[1]-benzopyrano[3,2-c]quinoline-6,7-(5H)-dione.

G. 5-cyclopropylmethyl-6H[1]-benzopyrano[3,2-c][1,8]naphthyridine-6,7-(5H)-dione.

H. 5-isopropyl-6H[1]-benzopyrano[3,2-c]quinoline-6,7-(5H)-dione.

I. 5-benzyl-6H[1]-benzopyrano[3,2-c]quinoline-6,7-(5H)-dione, m.p. 290°–292° C.

J. 2,5-dimethyl-6H[1]-benzopyrano[3,2-c]quinoline-6,7-(5H)-dione, m.p. 304°–307° C.

K. 5-(p-fluorobenzyl)-6H[1]-benzopyrano[3,2-c]quinoline-6,7-(5H)-dione.

L. 5-benzyl-6H[1]-benzopyrano[3,2-c][1,8]naphthyridine-6,7-(5H)-dione.

What is claimed is:

1. A compound of the formula:

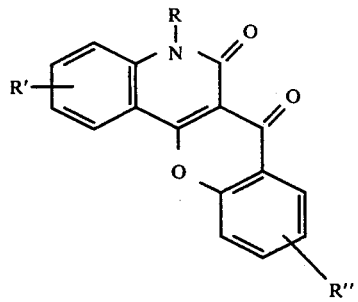

wherein

R is alkyl of 1 to 5 carbon atoms, alkenyl of 3 to 5 carbon atoms, alkynyl of 3 to 5 carbons, benzyl optionally mono- or disubstituted independently by fluoro, chloro or alkyl of 1 to 4 carbon atoms or cycloalkylalkyl in which the cycloalkyl is of 3 to 6 carbon atoms and the alkyl is of 1 to 3 carbon atoms, provided that the unsaturation on any alkenyl or alkynyl is other than on the alpha carbon atom, R' is hydrogen, alkyl of 1 to 4 carbon atoms, fluoro, chloro, bromo or alkoxy of 1 to 4 carbon atoms, and R'' is hydrogen or alkyl of 1 to 4 carbon atoms.

2. A compound of claim 1 in which R' is hydrogen.
3. A compound of claim 1 in which R'' is hydrogen.
4. The compound of claim 1 in which R is benzyl and R' and R'' are hydrogen.
5. A compound of claim 1 in which R is alkyl, alkenyl, alkynyl or cycloalkyl.
6. A compound of claim 1 in which R is alkyl, benzyl optionally monosubstituted by fluoro, chloro or methyl or cycloalkylalkyl.
7. A compound of claim 6 in which R is alkyl.
8. A compound of claim 1 in which R is alkyl.
9. The compound of claim 8 in which R is methyl and R' and R'' are hydrogen.
10. The compound of claim 8 in which R is ethyl and R' and R'' are hydrogen.
11. The compound of claim 8 in which R is isopropyl and R' and R'' are hydrogen.
12. A compound of claim 1 in which R is cycloalkylalkyl.
13. A compound of claim 11 in which R is cyclopropylmethyl.
14. The compound of claim 13 in which R' and R'' are hydrogen.

* * * * *